United States Patent [19]
Deutsch et al.

[11] Patent Number: 5,211,182
[45] Date of Patent: May 18, 1993

[54] HOME OVULATION TEST KIT AND METHOD

[76] Inventors: Marshall E. Deutsch, 41 Concord Rd., Sudbury, Mass. 01776; Stephen M. Blinn, 6 Thoreau Cir., Beverly, Mass. 01915

[21] Appl. No.: 781,842

[22] Filed: Oct. 23, 1991

[51] Int. Cl.⁵ ............................................. A61B 5/00
[52] U.S. Cl. ................................... 128/771; 604/318
[58] Field of Search .............. 128/760, 762, 771, 738; 206/569, 570; 604/317, 318

[56] References Cited

U.S. PATENT DOCUMENTS

| | | | |
|---|---|---|---|
| 3,037,496 | 6/1962 | Melges | 128/2 |
| 3,116,223 | 12/1963 | Rosner et al. | 436/65 X |
| 3,117,569 | 1/1964 | Wegner | 128/2 |
| 3,319,621 | 5/1967 | Schwerin | 128/771 |
| 3,406,015 | 10/1968 | Foster | 23/230 |
| 3,472,738 | 10/1969 | Foster | 436/65 X |
| 3,875,013 | 4/1975 | Manantou et al. | 435/200 X |
| 4,151,833 | 5/1979 | Polishuk | 128/738 |
| 4,349,632 | 9/1982 | Lyman et al. | 435/284 |
| 4,361,648 | 11/1982 | Chen | 422/56 X |
| 4,427,770 | 1/1984 | Chen et al. | 422/56 X |
| 4,580,577 | 4/1986 | O'Brien et al. | 128/760 |
| 4,635,488 | 1/1987 | Kremer | 128/771 |
| 4,713,165 | 12/1987 | Conouer et al. | 422/68 X |
| 4,770,856 | 9/1988 | Uthemann et al. | 436/165 X |
| 4,774,962 | 10/1988 | Hebel et al. | 128/760 |
| 5,022,409 | 6/1991 | Goldstein et al. | 128/760 |
| 5,056,521 | 10/1991 | Parsons et al. | 128/760 |
| 5,103,836 | 4/1992 | Goldstein et al. | 128/760 |

OTHER PUBLICATIONS

Prosser et al., Saliva and Breast Milk Composition During the menstral cycle of women Aust. J. Exp. Biol. Med. Sci. 61 (pt3) 265-275 (1983).
Scherstein "Screening for Bacteria . . . Glucose" 1968 vol. 204 No. 3.

*Primary Examiner*—Max Hindenburg
*Attorney, Agent, or Firm*—William Nitkin

[57] ABSTRACT

A testing kit and method for determining the day of ovulation in a woman who has menstruated having a plurality of test assemblies each with an upper chamber, a lower chamber in fluid communication with the upper chamber separated from the upper chamber by a screen member, a saliva-absorbable chewable plug which when chewed by the user can be compressed against the screen member to express saliva into the lower chamber which contains a reagent which produces a color change, the intensity of which is proportional to the concentration of glucose in the saliva wherein a plurality of such test assemblies are utilized one on each of successive days for determination of the peak color intensity on the day that the saliva has the greatest concentration of glucose to allow for computation from this peak day of the date of ovulation of the woman.

20 Claims, 4 Drawing Sheets

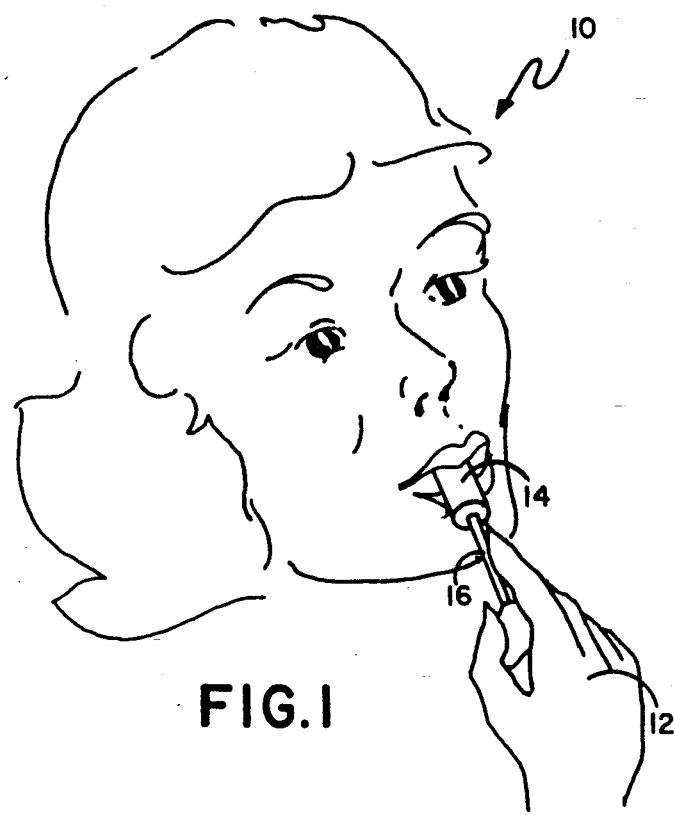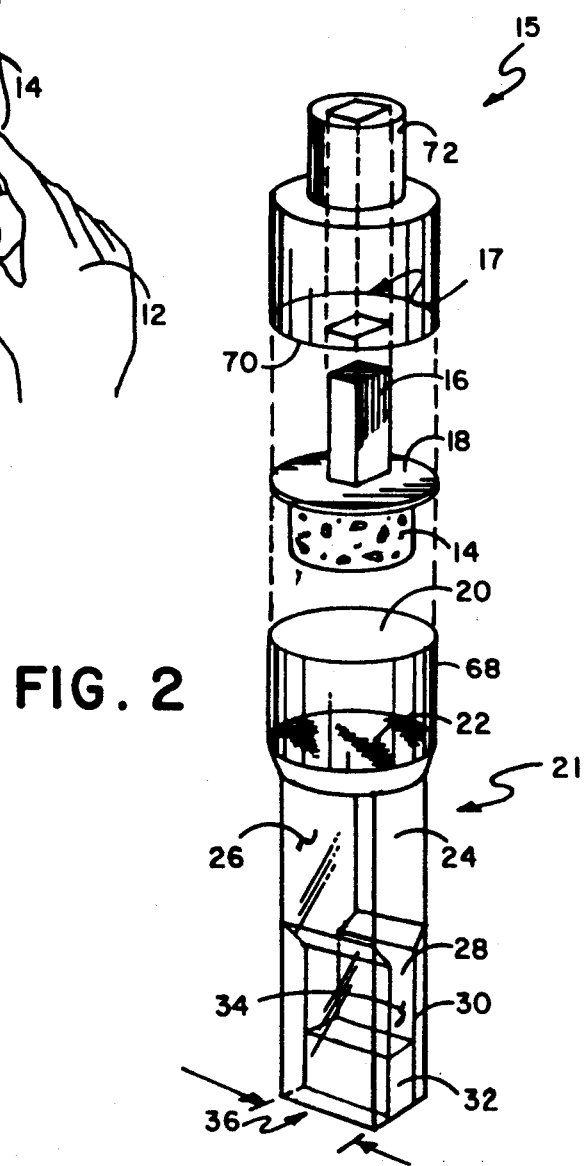

HOME OVULATION TEST KIT AND METHOD

BACKGROUND OF THE INVENTION

1. Field of the Invention

This invention concerns determination of the time of ovulation in women and more particularly relates to a home-testing kit easily used by women having no technical training to determine their day of ovulation.

2. Description of the Prior Art

Historically, ovulation time has been guessed on the basis of menstrual time or "mittelschmerz" (a sharp pain believed to be felt by some women at the moment of ovulation). More modern methods of determination include measurement of basal body temperature (taken before arising in the morning, where it shows a slight elevation at the time of ovulation) and, most notably and reliably, by determination of the urinary concentration of a hormone associated with ovulation.

Concentration of a specific enzyme in a body fluid is also a useful indicator. For example, Foster in U.S. Pat. No. 3,406,015 describes detection of the presence of peroxidase in the saliva of a woman. Wegner in U.S. Pat. No. 3,117,569 and Melges in U.S. Pat. No. 3,037,496 describe testing apparatus for detecting sugar in a woman's cervix using a "TESTAPE." French patent 2,305,161 describes detection of N-acetyl-beta-glucosaminidase in biological fluids.

Prosser et al in the Australian Journal Exp. Biol. Med. Sci. 61:265, 1983 describe elevation of glucose levels in saliva six days prior to ovulation. They state that "from a practical standpoint, an effective method of detecting the pre-ovulatory functional changes in the salivary gland may offer a convenient predictor of fertility in women."

SUMMARY OF THE INVENTION

This invention features a home-testing kit for determination of a day of ovulation in a woman. A testing kit is provided having a plurality of discrete, successive test assemblies, each containing a well holding a reagent suitable for colorimetric determination of glucose in saliva, wherein reaction of the reagent with glucose causes color formation proportional in intensity to glucose concentration. The woman obtains a first saliva sample on a first day of the use of the kit and places the first saliva sample in a first test assembly, as described in further detail below, to allow reaction of the reagent in the assembly's test well with the first saliva sample which resulting mixture is retained in the first test assembly. The woman provides a second saliva sample on the day following with the second saliva sample being deposited in the second test assembly to allow reaction of the reagent in the second assembly's test well with the resulting mixture also being retained in the second assembly's test well. On the next day a further saliva sample from the woman is obtained and is placed in the third assembly's test well to allow reaction of the reagent in the third assembly's test well with the resulting mixture being retained in the third assembly's test well. These steps continue using fresh test assemblies for each succeeding day through at least six days, and the user then compares the colors of the mixtures in the testing assembly wells and determines the day on which the test assembly's resulting mixture has the greatest color intensity. The day of ovulation is then determined by calculating six days after a day having such greatest color intensity.

Each test assembly in the kit includes a test well and a reagent containing glucose oxidase and peroxidase. The saliva sample can be as little as 0.1 ml but is optimally 0.25 ml of saliva. The test is started one week following menstruation. The test assemblies, when saliva has been entered therein, are held keyed into a base forming an array. The test assemblies should then be stored at a temperature below 10 degrees C. and sealed to prevent any evaporation of the mixture and saliva. The reagent described below is suitable for detecting a 0.1 millimolar level of glucose.

This invention features a kit, test assembly and method for determination of a day of ovulation in a woman which kit includes a plurality of test assemblies, each containing a region having the form of a test well sized and adapted for receiving a sample of saliva from the woman, and each region containing a reagent suitable for colorimetric determination of glucose concentration in saliva wherein reaction of the reagent with the glucose in the saliva causes color formation proportional in intensity to glucose concentration In the saliva.

The kit of this invention is a simple, relatively inexpensive and extremely easy-to-use device and method by which a woman can readily determine her date of ovulation. No other special apparatus or knowledge of chemistry is necessary. Further, the chemicals used in the reagent are safe in the hands of an inexperienced person. Since the use of the kit of this invention requires only a saliva sample which can be readily obtained with little effort, the invention herein provides a reliable and convenient method of determining the date of ovulation.

Other features and advantages of the invention will be apparent from the following description of the preferred embodiments thereof, and from the claims.

BRIEF DESCRIPTION OF THE DRAWINGS

FIG. 1 illustrates a woman chewing the chewable plug of one of the test assemblies of this invention to charge it with saliva.

FIG. 2 illustrates the parts of a test assembly.

DESCRIPTION OF THE PREFERRED EMBODIMENT(S)

Figure 3:
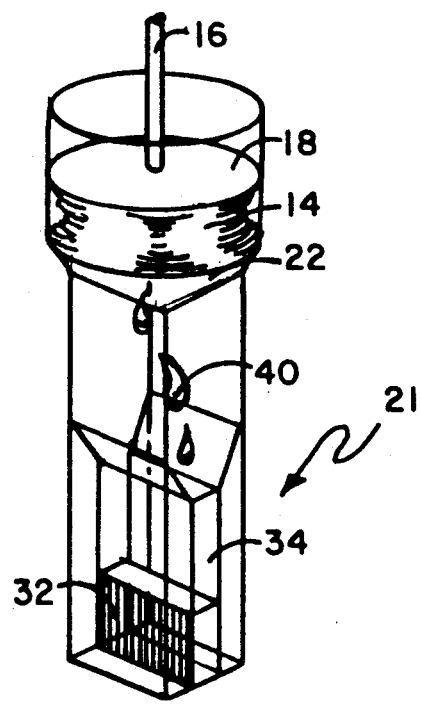
FIG. 3 illustrates the test assembly of FIG. 2 having the chewable plug compressed therein to force saliva through the test assembly screen into the test well at the base of the assembly.

FIG. 1 illustrates a woman 10 holding by hand 12 handle 16 upon which handle is mounted chewable plug 14 which can be made of sponge or other absorbent and compressible material that upon compression will express the saliva therefrom. Plug 14 can contain a sialagogue such as citric acid and a flavoring agent to promote salivation. The woman is illustrated chewing upon plug 14 to charge it full of saliva so that it can be used in test assembly 21 seen in FIG. 2. When chewable plug 14 is fully charged with saliva from chewing over a period of time, the plug is inserted into upper chamber 20 of test assembly 21 by handle 16 or by utilizing a handle receipt member 15 which will be further described below in the discussion of the alternate cap embodiments. Chewable plug 14 is positioned as seen in FIG. 2 by manual movement of plunger 18 on which the chewable plug is mounted into upper chamber 20 and is compressed against screen member 22. Upper chamber 20 has generally rounded walls 68 to accommodate a generally rounded chewable plug 14 as seen in the drawings. The saliva is forced by pressure of plunger 18, squeezing chewable plug 14, as seen in FIG. 3, against screen member 22 with drops of saliva 40 then passing through screen member 22 and dropping down into the lower chamber formed as a narrowed test well 30 in which reagent 32 is located as described below. It is desirable that the chewable plug be of a size to absorb enough saliva 40 such that when plunger 18 is forced against the chewable plug, at least 0.25–0.5 ml of saliva will be expressed and will fall down into the test well.

As seen in FIG. 2, lower chamber 24 is wider at its upper portion than at its lower portion and has sloping top well walls 28 which slant inward to narrow the chamber size such that saliva 40 falls into narrowed test well 30 and mixes with reagent 32. A well of smaller dimensions requires only a relatively small amount of saliva to complete the reaction with the reagent in the test well. A window member 34 on the front of each test well 30, which well can be 10 mm in cross-sectional length 36 from front to back, allows for the color of the resulting mixture to be viewed from the front of the test assembly. The cross-sectional length 36 is generally greater than the well's cross-sectional width. Each test well is of the same cross-sectional length and contains approximately the same amount of reagent. By viewing through window 34 from front to rear of each :est assembly, one can determine accurately the color intensity changes and thus the comparative levels of glucose present in the saliva of the test assemblies. Such results do not rely upon a specific amount of saliva being mixed with the reagent. The amount of saliva is not critical as long as a minimum amount is collected to mix with the reagent. There is more than sufficient reagent to react with all the glucose in the saliva sample. The color intensity is in proportion to the concentration of the glucose in the saliva and the depth of the well, which is constant, and not the amount of saliva. By using an excess of enzyme, each molecule of glucose in the saliva causes the conversion of one molecule of chromogen to a colored product.

Figure 4:
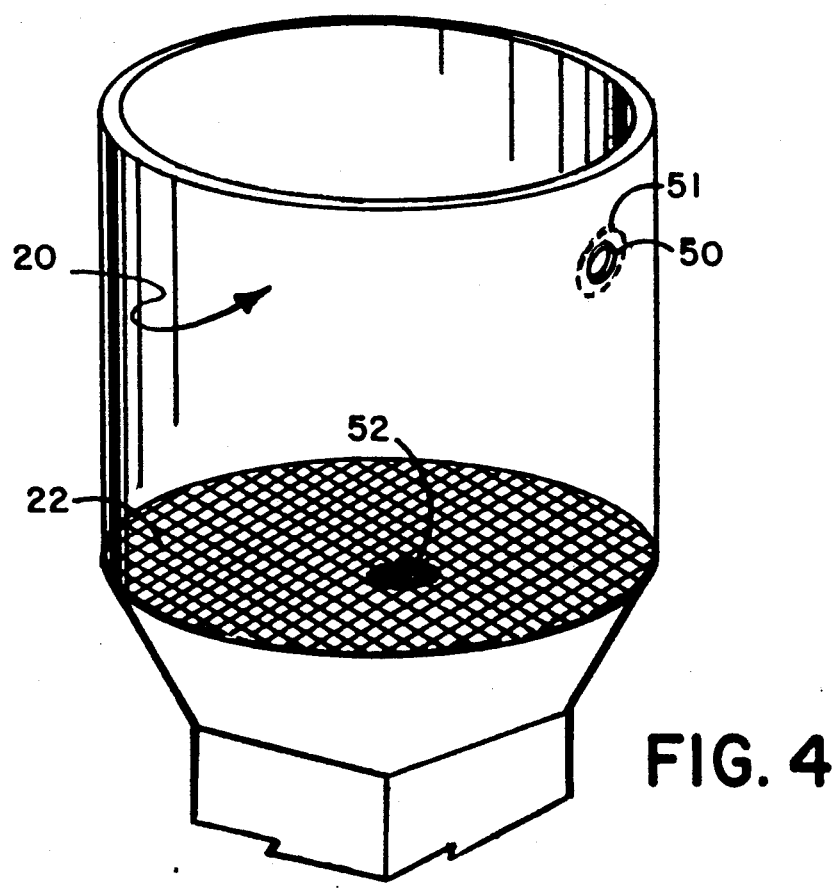
FIG. 4 illustrates an enlarged view of the upper chamber and screen of a test assembly.
Figure 7:
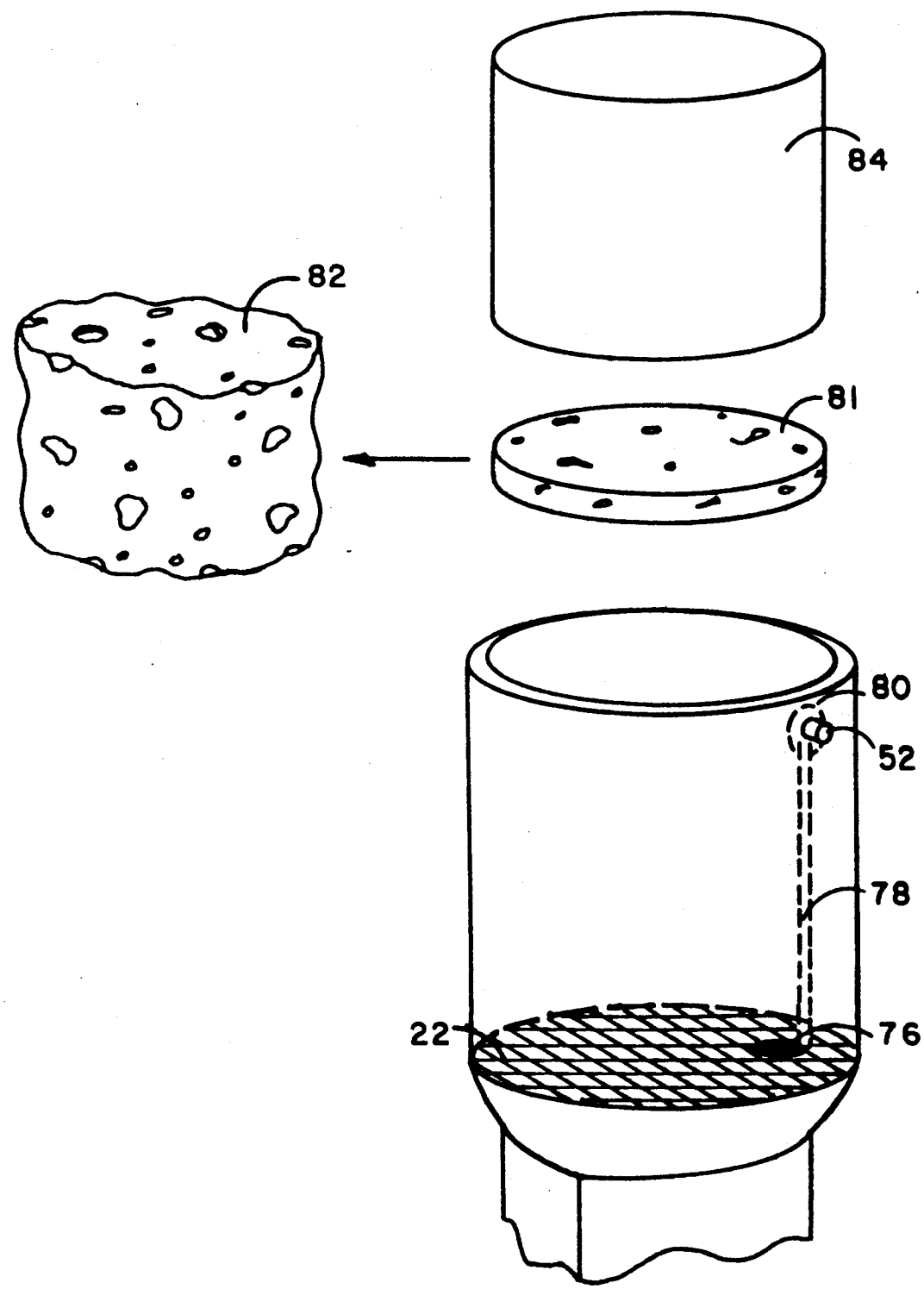
FIG. 7 illustrates an alternate embodiment of a chewable plug and air-venting system.

FIG. 4 illustrates upper chamber 20 and screen member 22 having an air vent 50 on the side to allow air to escape. Venting can be improved by having a silicone coating layer 51 around the edges of air vent 50 which layer helps the air to more easily escape from the chamber when the plug might otherwise block vent 50. Air bypass area 52 which can be on a central area of screen member 22 has a small spot of silicone coating placed thereon which is non-wettable which allows the air to escape past it but not the liquid, should any air be needed to be evacuated from the the lower chamber during the compression of the chewable plug against screen 22. Air bypass area 52 allows the saliva to more easily enter lower chamber 24 where it, by gravity, drops and slides on the sloped well edges down into the test well area 30 where it mixes with the reagent and eventually gels. In FIG. 7 an alternate air escape system is used. Silicon spot 76 is located near an edge of the upper chamber with a strip of silicone 78 extending up to air vent 52. The silicone strip extends around vent 52 forming a circle 80. This system allows the air to pass along the silicone strip which is non-wettable to air vent 52. An alternative to providing the air vent system above can include using a wider mesh screen member 22 with a small piece of filter paper or equivalent immediately above the reagent in the test well. The filter paper will cover and hold the reagent in place at the bottom of the well but will allow the saliva to pass therethrough after it is exposed into the assembly.

Figure 5:
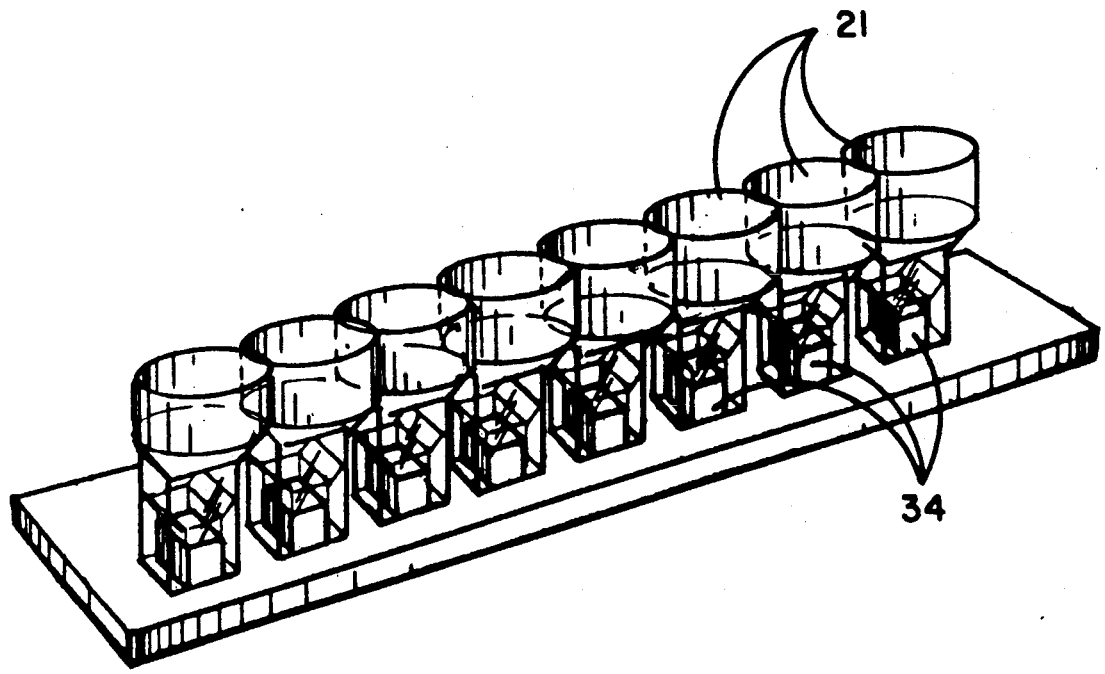
FIG. 5 illustrates a series of test assemblies keyed into a stand forming an array wherein the test assemblies are side-by-side having their window areas exposed in alignment with one another.

FIG. 5 illustrates the kit of this invention comprised of an array of test assemblies on stand 55 which can be made from a portion of the packaging of the box of the kit. There can be up to eight test assemblies, each of them being numbered consecutively by numbers 56, and they can be positioned and locked into the array by pressure of the stand against their bases, retaining them in position. The test assemblies when in the array are all aligned beside one another with the front windows arrayed parallel to one another so that they can be easily viewed for color intensity comparison by the user of the test kit of this invention.

In FIG. 2 handle receipt cap member 15 is illustrated which has a handle receipt slot 17 formed therein in which slot handle 16 can be retained. Base 70 of handle receipt cap member 15 is initially positioned in the test assembly's storage mode into the top of upper chamber 20, such base 70 being rounded to fit snugly so that it is retained in place. Plug 14 is positioned in upper chamber 20 with its handle 16 extending into handle receipt slot 17. In the test assembly's use mode one removes handle receipt cap member 15 to expose handle 16 then removed from handle receipt slot 17 for the user to grasp handle 16 and then to chew on the attached chewable plug 14 as seen in FIG. 1. Plug 14 is then returned into upper chamber 22. One can then reverse handle receipt cap member 15 which has slot 17 extending all the way to its upper portion 72 with handle 16 being then inserted into slot 17 of upper portion 72. The diameter of upper portion 72 is narrower than :he diameter of the body of the cap and is adapted to fit easily within the round walls 68 of upper chamber 20 so that handle receipt cap member 15 can then be used as a backing for plunger 18 similar to a piston. When narrow portion 72 of handle receipt cap member 15 is placed over handle 16 fitting into handle receipt slot 17 and cap member 15 is pushed downward, narrow portion 72 of handle receipt cap 15 fits inside the round walls 68 of upper chamber 20 causing chewable plug 14 to be compressed by manual force on the handle receipt cap so as to squeeze as much saliva as possible out of the chewable plug.

Figure 6:
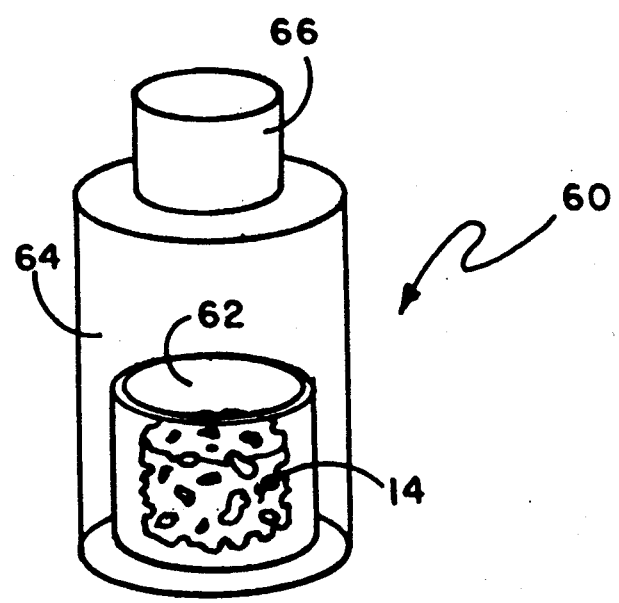
FIG. 6 illustrates an alternate cap structure for use in retention of the chewable plug and for expressing the saliva from the plug by compression in the upper chamber for the saliva to pass through the screen and fall into the test well below.

In an alternate embodiment of the handle receipt cap member, cap 60 is shown in FIG. 6, which is provided with a recess 62 in its bottom in which chewable plug 14 is inserted. In its storage mode cap 60 can be inserted and retained in upper chamber 20 seen in FIG. 2 until one desires to use the test assembly. One then removes cap 60 and pulls chewable plug 14 out of recess 62. After chewing the plug, one places the plug inside upper chamber 20 and then reverses the cap which has a narrower cap top portion 66 adapted to fit easily within upper chamber 20 and to be pushed downward, forcing the narrow cap top portion 66 of cap 60 on top of chewable plug 14, expressing the saliva therefrom and forcing it into lower chamber 24 where it will mix with reagent 32 within test well 30. FIG. 7 shows yet another type of plug 81 which in its unused mode can be compressed, flattened, dried and retained in its flattened state until it is chewed. A cap 84 can retain flattened plug 81 in place in the upper chamber. When plug 81 is chewed, the saliva causes it to expand into its in-use mode 82. Cap 84 can then be used to push chewed plug 82 against screen 22 in the upper chamber to express the saliva therefrom. The reagent in test well 30 should be a mixture of ingredients that will have a sensitivity to glucose concentrations and produce a color change when mixed with the saliva proportional to the concentration of glucose within the saliva sample. An example of such a reagent includes 4.4 mg citric acid monohydrate, 12.4 mg trisodium citrate dihydrate, 0.63 mg glucose oxidase, 0.48 mg peroxidase, 19 mg superclear gelatin (Knox Gelatine Company, Englewood Cliffs, N.J.), 2.85 micrograms 3-dimethylamino benzoic acid, and 11.1 micrograms 3-methyl-2-benzo-thiazolinone hydrazone. The citric acid and trisodium citrate can be replaced by any other suitable buffer, and the concentration of oxidase and peroxidase used can be reduced or increased as desired. The gelatin used can be replaced by any other clear gelling agent, such as agarose or agar agar, to produce a stable non-spillable reagent-/saliva mixture. The 3-dimethylamino benzoic acid and the hydrazone can also be replaced by other chromogens which yield a color representing the concentration of glucose in the saliva being tested. Ascorbic acid oxidase can be added to this reagent in order to reduce any interference by ascorbic acid which may be found in the saliva. Further, the reagent can be freeze-dried and the resulting powder held within the test wells. Preservatives to prevent microbial degradation, and stabilizers to enhance stability of the ingredients can also be added.

The following is an example of a method for use of the kit of this invention at home. Preferably, samples of saliva are obtained in the morning from a woman to be tested beginning a week after the onset of menstruation. The sample is preferably obtained before anything is taken by mouth such as food, toothpaste, mouthwash, medications, etc. If some substance is taken by mouth before the sample is obtained, a sample should be taken at least 20 minutes after such substance has been taken by mouth. The sample is taken as described below. On each day the kit is used, a test assembly for that day is chosen, the chewable plug is chewed, saliva is expressed through the screen into the test well and the test assembly is placed onto stand 55 in its numbered order. Each test assembly then forms part of the array for the color comparison checks as will be described further below. The array can be stored in a refrigerator between tests. However, before each sample of saliva is obtained the test assembly for use that day should be allowed to reach room temperature before its cap is removed.

The test is then repeated on successive days using a different test assembly each time. For example, on Day 2 saliva is added to the second test assembly and on Day 3 saliva is added to the third test assembly and so on for up to eight days. It should be noted that the objects of this invention could be theoretically accomplished over a three-day period should the day of greatest color intensity occur on the second day of testing, but the use of the kit over a longer period such as six to eight days allows for more leeway in determining the day of ovulation. Glucose in the saliva will react with reagent 32 to produce a blue color, the intensity of this color being dependent on the concentration of glucose in the saliva. The higher the concentration of glucose, the darker the blue color. Tests performed on successive days will yield progressively bluer colors for a few days. In later days, having reached a peak of maximum color intensity, the reaction will yield colors having less intensity for a few days. Six days after this day of maximum color intensity represents the day of ovulation.

It is preferred, if ascorbic acid oxidase is not incorporated into the reagent, during use of this test that dietary supplements of vitamin C in excess of 15 mg per day not be consumed, and that no mo citrus fruit or tomato juice be ingested per day. The reason for this requirement is that excessive amounts of vitamin C may interfere with the test.

Although the present invention has been described with reference to particular embodiments, it will be apparent to those skilled in the art that variations and modifications can be substituted therefor without departing from the principles and spirit of the invention.

We claim:

1. A test array for viewing and making colorimetric determinations of a scheduled series of reactions comprising:
an array of test assemblies, each test assembly including:
an upper chamber;
a lower chamber in fluid communication with said upper chamber, said lower chamber having a predetermined cross-sectional length and cross-sectional width;
transparent window means in said lower chamber for unaided viewing of any contents thereof;
a screen member positioned between said upper chamber and said lower chamber;
a fluid-absorbable chewable plug member removably positioned within said upper chamber, said plug member absorbing such fluid as is to be colorimetrically evaluated;
means for compression of said plug member after absorbing fluid and when positioned within said upper chamber to express said fluid from said plug member through said screen member into said lower chamber; and
a reagent disposed in said lower chamber capable of producing a colored reaction product after admixture with any of said fluid expressed from said plug member, said colored reaction product being viewed unaided through said window means of said lower chamber when making a colorimetric determination,
said array of test assemblies providing a viewable range of colored reaction products of specific intensities correlatable with the scheduled series of reactions.

2. The test array of claim 1 wherein said test is for determining the day of peak ovulation of a woman; wherein said fluid is saliva obtained from a woman chewing said chewable plug; and wherein one of said test assemblies is utilized per day over a series of successive days.

3. The test array of claim 2 wherein a series of between three to eight test assemblies are utilized in said array, one each utilized on successive days and further wherein said reagent contains a glucose oxidase enzyme and a peroxidase which reagent, when saliva is added thereto, produces a color with the intensity of the color being proportional to the concentration of glucose in said saliva with the most intense color produced on the day of greatest glucose concentration in the saliva.

4. The test array of claim 3 wherein there is an excess of reagent sufficient to react with all of the glucose in said saliva, said reaction being independent of the amount of saliva deposited in said test assembly.

5. The test array of claim 4 wherein said means for viewing the contents of the lower chamber of each test assembly comprises a transparent window aligned with the cross-sectional length of said lower chamber to allow viewing of said reagent/saliva mixture through said entire cross-sectional length for color intensity comparison of the contents of said lower chamber of different test assemblies.

6. A test assembly for viewing and making a colorimetric determination comprising:
an upper chamber;
a lower chamber in fluid communication with said upper chamber, said lower chamber having a predetermined cross-sectional length and cross-sectional width;
transparent window means in said lower chamber for unaided viewing of any contents thereof;
a screen member disposed between said upper chamber and said lower chamber;
a fluid-absorbable chewable plug member removably positioned within said upper chamber, said plug member absorbing such fluid as is to be colorimetrically evaluated;
means for compression of said plug member after absorbing fluid and when positioned in said upper chamber to express said fluid from said plug member through said screen member into said lower chamber; and
a reagent disposed in said lower chamber capable of producing a colored reaction product after admixture with the fluid expressed from said plug member, said colored reaction product being viewed unaided through said window means of said lower chamber when making a colorimetric determination.

7. The test assembly of claim 6 wherein said fluid is saliva and said test assembly is used for testing glucose concentration in said saliva for determination of the day of ovulation in a woman who has menstruated.

8. The test assembly of claim 7 wherein the screen member between said upper and lower chambers retains said plug within said upper chamber while allowing the saliva to pass through the openings in said screen member to react with said reagent in said lower chamber.

9. The test assembly of claim 8 wherein there is an excess of reagent over the amount needed to react with all of the glucose in the saliva causing the entire amount of glucose to react with the reagent and produce a color change with the intensity of the color produced proportional to the concentration of glucose in the saliva, such color intensity visible through said transparent wall throughout the cross-sectional length of said lower chamber, said color intensity being unaffected by the amount of saliva in said lower chamber but controlled solely by the concentration of glucose in the saliva, creating a colorimetric determination test independent of the amount of saliva in said lower chamber.

10. The test assembly of claim 9 wherein said reagent further includes a gelling agent.

11. The test assembly of claim 10 wherein said plug member is chewed and absorbs saliva and wherein said plug member contains a sialagogue to promote salivation.

12. The test assembly of claim 11 further including means to allow air escape from said lower chamber as said saliva is being expressed through said screen member by said means for compression.

13. The test assembly of claim 12 wherein said lower chamber is generally rectangular in configuration and said upper chamber is of an open-topped cylindrical configuration.

14. A method for viewing and making a colorimetric determination comprising the steps of:
introducing fluid into a fluid-absorbable plug such that said fluid is releasably absorbed by said plug;
inserting said fluid-absorbed plug into a test assembly comprising:
an upper chamber,
a lower chamber in fluid communication with said upper chamber, said lower chamber having a predetermined cross-sectional length and cross-sectional width,
window means in said lower chamber for unaided viewing of any contents thereof,
a screen member positioned between said upper chamber and said lower chamber,
means for compression of said fluid-absorbed plug member within said upper chamber to express said fluid from said plug member through said screen into said lower chamber, and
a reagent disposed in said lower chamber capable of producing a colored reaction product after admixture with any of said fluid expressed from said plug member, said colored reaction product being viewed unaided through said window means of said lower chamber when making a colorimetric determination;
compressing said plug member against said screen member;
expressing the fluid from said plug member through said screen member into said lower chamber;
allowing said reagent in said lower chamber to react with said fluid to produce colored reaction product of a specific intensity; and
viewing the intensity of said colored reaction product through said window means of said lower chamber.

15. A method for determining the date of a woman's ovulation by viewing and making a colorimetric determination over successive test days, said method comprising the steps of:
determining a first test day occurring one week after onset of the woman's menstruation; then
colorimetrically evaluating the glucose in the saliva of the woman said first test day and repeatedly on each of the successive test days thereafter by
(a) chewing a saliva-absorbing plug by the woman on each of said test days such that the woman's saliva is releasably absorbed by said plug;
(b) inserting said saliva absorbed plug of each test day into an individual test assembly in an array of test assemblies, each test assembly of said array comprising:
an upper chamber;
a lower chamber in fluid communication with said upper chamber, said lower chamber having a predetermined cross-sectional length and cross-sectional width, window means in said lower chamber for unaided viewing of any contents thereof, a screen member positioned between said upper chamber and said lower chamber, means for compression of said saliva absorbed plug within said upper chamber to express said saliva from said plug member through said screen member into said lower chamber, a reagent disposed in said lower chamber capable of reacting with glucose in said saliva, said reagent having a concentration greater than the amount needed to react with all of said glucose to produce a colored reaction product whose intensity is proportional to the concentration of glucose in said saliva, the intensity of said colored reaction product being viewed unaided through said window means of said lower chamber when making a colorimetric determination, (c) compressing said saliva absorbed plug of each test day against said screen member;

(d) expressing the saliva from said plug of each test day through said screen member into said lower chamber; and (e) allowing said reagent in said lower chamber to react with said saliva of each test day to produce a colored reaction product of a specific intensity; then retaining said colored reaction product of each test assembly in said array for each of said test days;

viewing the intensity of each colored reaction product through said window means of said lower chamber in each test assembly in said array for each of said test days; and comparing the color intensity of each colored reaction product in each test assembly in said array to determine which of said test days yielded the greatest concentration of glucose in the saliva and was the day of ovulation for the woman.

16. A testing kit for viewing and making a colorimetric determination of the day of ovulation in a woman who has menstruated, said testing kit comprising:

a base;

a plurality of test assemblies each for use on successive test days starting one week after the onset of menstruation, said test assemblies positioned on said base, each test assembly including:

an upper chamber;

a lower chamber in fluid communication with said upper chamber, said lower chamber of a predetermined cross-sectional length and cross-sectional width;

transparent window means in said lower chamber for unaided viewing of any contents thereof through said cross-sectional length;

a screen member disposed between said upper chamber and said lower chamber;

a saliva-absorbable chewable plug member removably positioned within said upper chamber, said plug member to be chewed by said woman;

means for compression of said plug member after absorbing saliva and when positioned within said upper chamber to express said saliva from said plug member through said screen member into said lower chamber; and a reagent disposed in said lower chamber capable of producing a colored reaction product after admixture with the saliva expressed from said plug member, said colored reaction product being viewed unaided through said window means of said lower chamber when making a colorimetric determination, the amount of said reagent being in excess over the amount of glucose in said saliva to produce a colored reaction product wherein the intensity of the color produced is proportional to the concentration of glucose in the saliva, said plurality of test assemblies providing a viewable range of colored reaction products of specific intensities by which to determine the day of ovulation.

17. The testing kit of claim 16 wherein said reagent further includes a gelling agent.

18. the testing kit of claim 16 wherein said plug member contains a sialagogue to promote salivation.

19. The testing kit of claim 16 further including means to allow air escape from said lower chamber as said saliva is being expressed through said screen member by said means for compression.

20. The testing kit of claim 16 wherein such color intensity visible through said transparent window means through said cross-sectional length of said lower chamber is unaffected by the amount of saliva expressed into said lower chamber but such color intensity is controlled solely by the concentration of glucose in said saliva, creating a colorimetric determination testing kit independent of the amount of saliva in said lower chamber wherein the user of said kit determines the date of ovulation based on computation from the date of greatest color intensity of the reagent/saliva mixture.

* * * * *